United States Patent [19]

Davis

[11] 4,196,851

[45] Apr. 8, 1980

[54] SCENTED SACHET TABLET

[75] Inventor: Robert D. Davis, Hazelwood, Mo.

[73] Assignee: Treasure Masters Corp., Derry, N.H.

[21] Appl. No.: 943,764

[22] Filed: Sep. 20, 1978

[51] Int. Cl.² ........................... A61K 7/46; C11B 9/00
[52] U.S. Cl. ................................. 239/54; 252/522 A; 252/428
[58] Field of Search ................... 252/522, 428; 239/54

[56] References Cited

U.S. PATENT DOCUMENTS

| | | | |
|---|---|---|---|
| 2,564,860 | 8/1951 | Ryberg | 239/54 |
| 3,261,746 | 7/1966 | Copley | 252/522 A |
| 4,128,508 | 12/1978 | Munden | 252/522 A |

*Primary Examiner*—Veronica O'Keefe

*Attorney, Agent, or Firm*—Strimbeck Professional Association

[57] ABSTRACT

A porous sachet tablet prepared by compression molding or tableting a powder composed of insoluble tribasic calcium phosphate mixed with a minor amount of soluble sodium hexametaphosphate and bonded with a small amount of food starch and internally lubricated with a fatty acid soap, preferably magnesium stearate, to aid tableting. This tablet or blank is preferably prepared by slurrying the phosphates and the binder in water, spray drying the slurry, dry-mixing in the lubricant and compression molding. The tablet is then wetted with a perfume of the desired fragrance to give the sachet tablet.

3 Claims, No Drawings

SCENTED SACHET TABLET

This invention is concerned with the manufacture of a fragrance-carrying tablet or blank to be used in sachets. As compared to earlier manufactures it is harder and more crushresistant, has a more uniform porosity, presents a larger available internal surface area, absorbs a greater amount of perfume, and retains the fragrance longer, i.e. more slowly and uniformly releases the fragrance such that the tablet has a greater effective life. The tablet does not react with or alter the scent of the perfume.

In brief compass, the tablet or pill of this invention comprises a mixture of a major amount of insoluble tri-basic calcium phosphate with minor amounts of water soluble sodium hexamethaphosphate, a food starch binder and a fatty acid soap internal lubricant used as an aid to compression molding. The phosphates and the binder are preferably slurried in water, spray dried to a powder, the lubricant is added, and the powder is compression molded to yield the tablet. The tablet is then used to absorb a perfume, preferably one that is alcohol based.

The scented tablet is normally used by inserting it in a small pillow, in a handkerchief box, in a small bag, or the like, which items then may be used to scent drawers or closets.

The nature of this invention and its advantages are further explained in the following description which gives an example of a presently preferred way of practicing the invention.

EXAMPLE

| Composition | | |
|---|---|---|
| | Weight Percent, Dry Basis | |
| | Range | Example |
| $Ca_3(PO_4)_2$ | Balance | 82 |
| Binder | 5 to 20 | 10 |
| $Na\ PO_3$ | 5 to 10 | 7 |
| Lubricant | 1 to 2 | 1 |
| Slurry water content | 40 to 55 | 45 |
| Powder water content | less than 3 | 2 |

The slurry is prepared in a mixer (Littleford Lodige Mixer). The phosphates and the food starch (Capsule 51-5329 by National Starch and Chemical Corp.) are first mixed and dissolved in water and the slurry is then spray dried to give a dry powder. For example, a modified Coulter type 6 foot diameter co-current gas fired spray dryer with inlet heat 320° F., outlet 190° F., Nozzle SC120@600 PSI running at a capacity of 210 Kg. per hour was used to produce a powder of generally spherical particles having a moisture content of about 2 weight percent and a size distribution of 42% through 14 mesh and over 60 mesh, 21% through 60 mesh and over 100 mesh, 19% through 100 mesh and over 170 mesh screens.

Tablets can be prepared having the shape and size desired in a tableting machine. For example, a BB-2 Stokes tableting machine was used to produce dull white tablets or blanks 1½ centimeters in diameter and 4 millimeters thick with slightly rounded ends out of the powder of the example after the magnesium stearate lubricant was blended in. Each tablet had a weight of 915 mgms. Tablet weights for sachets will normally be in the range of 800 to 1000 mgms. (milligrams).

A suitable dye, such as Red F5RK can be added to the water slurry to impart such color to the tablets as may be desired.

Scented tablets were produced from the tablets of the Example by mixing with an alcohol based perfume known as Woodsprite (My Treasure). The perfume oil is added to the tablet by soaking in the perfume oil for about 35 minutes, following which the tablets were spread out and dried. Each tablet contained about 0.2 grams of perfume oil. Water based perfumes can also be used.

The tablets so prepared did not alter or interfere with the fragrance and slowly released the fragrance over a long period of time. The tablets held more perfume than those of earlier manufacture, approximately 12 weight percent more, which indicates that the porosity particle uniformity and available internal surface area have been improved. The tablets were decidedly more crush-resistant.

The phosphate powder for tableting can also be prepared by extrusion of a phosphate/binder/water paste having a higher solids content than the slurry, followed by drying of the extrudate and particulization as by ginding. This method so far is less preferred as the particle shape and size distribution are different.

The tri basic calcium phosphate is unique for applicant's purposes and while other type of binders may be used, the modified starch is definitely preferred.

What is claimed is:

1. A sachet tablet comprising:

| | Weight Percent |
|---|---|
| $Ca_3(PO_4)_2$ | Balance |
| Modified food starch (binder) | 5 to 20 |
| Sodium hexametaphosphate | 5 to 10 |
| Fatty acid soap | 1 to 2 | said tablet being prepared by mixing the phosphates and binder in water, drying and particulating, dry mixing in said fatty acid soap in powder form, and compression molding to yield said tablet.

2. The tablet of claim 1 wherein said tablet is wetted with a perfume and dried to yield a scented tablet.

3. The tablet of claim 1 wherein said tablet is prepared by slurrying the phosphates and binder with water, spray drying the slurry to less than 3 weight percent water content to obtain a powder, adding said fatty acid soap and tableting the powder to produce a tablet having weight in the range of 800 to 1000 grams.

* * * * *